(12) United States Patent
Ardavan et al.

(10) Patent No.: US 11,653,566 B2
(45) Date of Patent: May 16, 2023

(54) MOLECULAR ELECTRONIC DEVICE (71) Applicant: Oxford University Innovation Limited, Oxford (GB)

(72) Inventors: Arzhang Ardavan, Oxford (GB); Andrew J. Turberfield, Oxford (GB); Richard E. P. Winpenny, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 15/734,372

(22) PCT Filed: Jun. 5, 2019

(86) PCT No.: PCT/GB2019/051563
§ 371 (c)(1),
(2) Date: Dec. 2, 2020

(87) PCT Pub. No.: WO2019/234427
PCT Pub. Date: Dec. 12, 2019

(65) Prior Publication Data
US 2021/0175445 A1    Jun. 10, 2021

(30) Foreign Application Priority Data
Jun. 5, 2018    (GB) ..................................... 1809207

(51) Int. Cl.
*H01L 51/00* (2006.01)
*H01L 51/05* (2006.01)
*H01L 51/10* (2006.01)

(52) U.S. Cl.
CPC ...... *H01L 51/0093* (2013.01); *H01L 51/0003* (2013.01); *H01L 51/0595* (2013.01); *H01L 51/102* (2013.01)

(58) Field of Classification Search
CPC .................... H01L 51/0098; H01L 51/0595
See application file for complete search history.

(56) References Cited

U.S. PATENT DOCUMENTS

2003/0077625 A1    4/2003    Hutchison
2005/0015351 A1*   1/2005    Nugent ................. G06N 3/063
                                                706/33

(Continued)

FOREIGN PATENT DOCUMENTS

KR    2016 0094914 A    8/2016
WO    96/30508 A1       10/1996

(Continued)

OTHER PUBLICATIONS https://en.wikipedia.org/wiki/DNA.*

(Continued)

*Primary Examiner* — Jae Lee
(74) *Attorney, Agent, or Firm* — Thomas|Horstemeyer, LLP (57) ABSTRACT

A molecular electronic device (10) includes a framework of polynucleotides (3), one or more molecular electronic components (4) and one or more electrical contacts (7). The molecular electronic components and the electrical contacts are each connected to the plurality of polynucleotides such that the molecular electronic components and the electrical contacts are located with respect to the framework and with respect to each other. This forms a coupling between the electrical contacts and the molecular electronic components.

20 Claims, 4 Drawing Sheets

(56) References Cited

U.S. PATENT DOCUMENTS

| | | | | |
|---|---|---|---|---|
| 2011/0275062 A1* | 11/2011 | Guo | ................ | G01N 33/54373 |
| | | | | 435/6.1 |
| 2016/0053300 A1* | 2/2016 | Maglia | ................ | C07K 14/255 |
| | | | | 435/6.1 |

FOREIGN PATENT DOCUMENTS

| | | |
|---|---|---|
| WO | 03/041182 A2 | 5/2003 |
| WO | 2017/123416 A1 | 7/2017 |

OTHER PUBLICATIONS

International Search Report & Written Opinion for WO2019/234427 (PCT/GB2019/051563), dated Aug. 22, 2019, pp. 1-14.

UK Search Report for GB1809207.2, dated Oct. 31, 2018, pp. 1-4.

"Fault tolerant design and analysis of carbon nanotube circuits affixed on DNA origami tiles" E Czeizler, IEEE Transactions on Nanotechnology, vol. 14, No. 5, Sep. 2015.

"Nano and micro-assembly of molecular components by means of nucleic acid hybridization" CM Niemeyer, Proc. Int. Conf. on Microtechnologies, 25/9/200, vol. 1, pp. 45-47.

"DNA based molecular technology", A Czaki et al., Single Molecules, vol. 3, pp. 275-280, 2002.

European Office Action for Application No. 19730501.4, dated Apr. 28, 2022, pp. 1-6.

International Preliminary Report on Patentability for WO2019/234427 (PCT/GB2019/051563), dated Dec. 8, 2020, pp. 1-8.

\* cited by examiner

MOLECULAR ELECTRONIC DEVICE

CROSS-REFERENCE TO RELATED APPLICATIONS

This application is the National Stage of International Application No. PCT/GB2019/051563, filed Jun. 5, 2019, which claims priority to GB 1809207.2, filed Jun. 5, 2018, which are entirely incorporated herein by reference.

This invention relates to a molecular electronic device and a method of assembling a molecular electronic device.

Molecules (e.g. having a defined atomic composition and structural formula) are the smallest objects that can be manipulated for their function. Molecular electronic components therefore provide the ultimate limit for miniaturising electrical circuits. At this scale, quantum phenomena dominate the properties of such devices and so molecular electronic components may be able to be used to investigate the development of components for quantum technologies.

However, owing to their size (typically smaller than the smallest metal wire that is possible to fabricate), it is difficult to manipulate molecular electronic components to connect them into electrical circuits and the yields obtained using conventional engineering methods are very low.

In one technique, a gap of a few nanometres can be made in a thin wire (known as a "break junction"), using an electrical current or mechanical strain. Molecular components can then be deposited on the wire, hoping that one (and only one) bridges the gap in the wire, such that the component can then be incorporated into a circuit. However, this technique relies on chance and so rarely yields a working device. Furthermore, because it is not possible to control the shape of the gap in the wire and the orientation of the molecule relative to the wire with any precision, it is rare for such "working" devices to exhibit reproducible properties.

In another technique, a scanning tunneling microscope can be used to locate and investigate molecular components that are deposited on a conducting surface. This process is more reliable and repeatable than inserting a molecular component into a break junction. However, this technique uses bulky experimental apparatus which limits the geometry that can be used for molecular electronic devices, ruling out some practical devices.

The aim of the present invention is to provide an improved molecular electronic device and a method of assembling a molecular electronic device.

When viewed from a first aspect the invention provides a molecular electronic device comprising:
 a framework comprising a plurality of polynucleotides;
 one or more molecular electronic components; and
 one or more electrical contacts;
 wherein the one or more molecular electronic components and the one or more electrical contacts are each connected to one or more of the plurality of polynucleotides such that the one or more molecular electronic components and the one or more electrical contacts are located with respect to the framework and with respect to each other so as to form a coupling between the one or more electrical contacts and the one or more molecular electronic components.

When viewed from a second aspect the invention provides a method of assembling a molecular electronic device, the method comprising:
 assembling a framework from a plurality of polynucleotides;
 connecting one or more molecular electronic components to one or more of the plurality of polynucleotides; and
 connecting one or more electrical contacts to one or more of the plurality of polynucleotides;
 wherein the one or more molecular electronic components and the one or more electrical contacts are each connected to one or more of the plurality of polynucleotides such that the one or more molecular electronic components and the one or more electrical contacts are located with respect to the framework and with respect to each other so as to form a coupling between the one or more electrical contacts and the one or more molecular electronic components.

When viewed from a third aspect the invention provides a molecular electronic device obtainable by a method as outlined in the second aspect of the invention.

The present invention provides a molecular electronic device and a method of assembling a molecular electronic device. The device includes a framework that is assembled from multiple polynucleotides (e.g. through the hybridization of pairs of polynucleotides to form double helices). One or more molecular electronic components and one or more electrical contacts are located with respect (e.g. connected) to the polynucleotide framework. The one or more electrical contacts are also located with respect to the one or more molecular electronic components.

The electrical contact(s) and the molecular electronic component(s) are located with respect to the framework and to each other by connecting each of them to one or more polynucleotides forming the framework. The location of the electrical contact(s) and the molecular electronic component(s) with respect to the framework and to each other, e.g. when the framework is assembled, is such that couplings (such as electrical connections) are formed between the electrical contact(s) and the molecular electronic component(s), to form the molecular electronic device.

Similarly, when the device comprises multiple molecular electronic components, preferably couplings are formed between (e.g. pairs of) the molecular electronic components in the same way. Thus, in a preferred embodiment, the molecular electronic device comprises a plurality of molecular electronic components, and the plurality of molecular electronic components are each connected to one or more of the plurality of polynucleotides such that two or more of the plurality of molecular electronic components are located with respect to the framework and with respect to each other so as to form a coupling between the two or more molecular electronic components.

Thus it will be appreciated that by using polynucleotide (e.g. DNA nanotechnology) techniques to create a framework and to connect the molecular electronic component(s) and the electrical contact(s) to the polynucleotides to locate them with respect to the framework (and to each other), in at least preferred embodiments this helps to allow the molecular electronic component(s) and the electrical contact(s) to be positioned reliably and accurately with respect to each other, owing to the hybridization between complementary bases of the polynucleotides to form the framework. This relative locating of the different constituent parts with respect to each other allows couplings between the molecular electronic component(s) and the electrical contact(s)), and e.g. between multiple (e.g. pairs of) molecular electronic components, to be formed.

The use of a polynucleotide framework to locate the electrical contact(s) and the molecular electronic component(s) also helps to ensure that only one component is located at each desired site on the framework. This helps to avoid problems caused by the binding of multiple components in, for example, a break junction.

The coupling between the molecular electronic component(s) and the electrical contact(s) (and, e.g., between multiple (e.g. pairs of) molecular electronic components), as part of the formation of the molecular electronic device, thus provides a wired up device (e.g. a single molecular transistor or diode, or an integrated circuit comprising multiple such circuit elements), which may then allow the molecular electronic component(s) to be connected to external circuitry through external electrical connection(s) to the electrical contact(s). The molecular electronic device can thus be "wired up", e.g. as part of a circuit, allowing the molecular electronic component to be used (e.g. its function controlled). This helps to overcome the problems of prior techniques in being able to locate electrical contacts with respect to molecular electronic components in a reliable and accurate manner such that the molecular electronic components can be connected up into larger electrical circuits.

Using polynucleotides (e.g. deoxyribonucleic acid (DNA)) also has the advantages that the properties of such polynucleotides can be exploited. For example, polynucleotides are inherently stable and so can be dried out while retaining their structure (e.g. of the framework). This may allow the molecular electronic device to be connected as part of a larger circuit while retaining the relationship of the constituent parts of the molecular electronic device with respect to each other. Polynucleotides also have little intrinsic electrical conductivity so help to provide the necessary structure for the framework in the molecular electronic device while not interfering with the electronic function of the device.

Assembling a molecular electronic device in this way may therefore be more reliable than conventional techniques, thus helping to allow working devices to be produced with confidence. It may also be more repeatable than conventional techniques, thus helping to allow the yield of molecular electronic devices assembled in this way to be improved. Furthermore, owing to the ability to synthesise specific polynucleotide sequences, such molecular electronic devices may be able to be built to a specific design.

The framework, when assembled from the plurality of polynucleotides, may comprise any suitable and desired (e.g. one-dimensional, two-dimensional or three-dimensional) structure. In one embodiment the framework comprises an (e.g. parallel) array of polynucleotide helices, preferably assembled using the DNA "origami" or the DNA "bricks" technique. The framework may comprise a single layer of double stranded polynucleotide helices but preferably the framework comprises a plurality of layers of double stranded polynucleotide helices. The number of layers of the framework may be used to control the spacing of the molecular electronic component from the contact(s) and, e.g., the spacing of the contacts from each other when the molecular electronic device comprises more than one contact.

The framework may comprise any suitable and desired type of polynucleotides (e.g. synthetic, genomic or modified genomic deoxyribonucleic acid (DNA) or ribonucleic acid (RNA), or nucleic acid analogue such as peptide nucleic acid (PNA), locked nucleic acid (LNA), glycol nucleic acid (GNA), etc.).

In one embodiment the plurality of polynucleotides comprises a plurality of shorter polynucleotides. Such polynucleotides may form most or all of the structure forming the framework and help to link, e.g., different layers forming the framework together, e.g. using the DNA "bricks" technique. Preferably the shorter polynucleotides (e.g. each) have a total length of fewer than 100 nucleotides, e.g. fewer than 50 nucleotides.

In one embodiment the plurality of polynucleotides comprises a longer polynucleotide. Preferably the longer polynucleotide comprises greater than 100 nucleotides, e.g. greater than 1000 nucleotides.

In a particularly preferred embodiment the plurality of polynucleotides comprises both a longer polynucleotide and a plurality of shorter polynucleotides. Preferably the longer polynucleotide forms a "scaffold" polynucleotide that runs through the framework and, e.g., is "stapled" together using the shorter polynucleotides, e.g. as used in the DNA "origami" assembly technique.

Thus, in a particularly preferred embodiment the framework comprises a longer polynucleotide and a plurality of shorter polynucleotides, wherein the plurality of shorter polynucleotides are arranged to link together different parts of the longer "scaffold" polynucleotide, e.g. to form an array of double stranded polynucleotide helices. Preferably the method comprises assembling the framework by linking together different parts of the longer polynucleotide using the plurality of shorter polynucleotides.

Owing to the predictable hybridization of complementary sections of polynucleotides to form a double helix, polynucleotides may be formed (e.g. synthesized) that will hybridize such that they assemble into the desired structure for the framework.

In one embodiment the plurality of polynucleotides comprises natural sequences of polynucleotides, e.g. for the "scaffold" polynucleotide. In one embodiment the plurality of polynucleotides comprises synthesised sequences of nucleotides, e.g. for the polynucleotide "staples" (and/or the "scaffold" polynucleotide). Thus, in one set of embodiments the method comprises (e.g. designing and) synthesising (at least some of) the plurality of polynucleotides.

The framework may be any suitable and desired size. In one embodiment the framework has a maximum dimension of between 50 nm and 200 nm, e.g. approximately 100 nm. It will be appreciated that double-stranded polynucleotides are stiff over a length of ~50 nm. This helps in the construction of a (e.g. fully defined) framework of the order of hundreds of nanometres, thus helping to control the geometry and nature of the molecular electronic device, e.g. in arranging the position of its constituent parts (e.g. molecular electronic component(s) and contact(s)) with respect to each other.

Preferably the method comprises annealing the plurality of polynucleotides (e.g. the polynucleotide "scaffold" and the plurality of polynucleotide staples) to assemble the framework. Thus preferably the assembled framework comprises substantially double stranded polynucleotide helices (e.g. apart from single-stranded sections of polynucleotide(s) to be used to locate the contact(s) and the molecular electronic component(s)). As will be discussed below, the contact(s) and the molecular electronic component(s) may be connected to the framework, and/or located with respect to each other (to form the coupling(s) therebetween), in this same annealing step, or once the plurality of polynucleotides have been annealed to form the framework.

Preferably the framework comprises one or more (e.g. a plurality of) polynucleotides having single-stranded sections, e.g. when the framework is (or has been) assembled. These polynucleotides with single-stranded sections (i.e. that do not hybridize with other polynucleotides forming the framework) may be used to attach to complementary polynucleotides for connecting the molecular component(s) and the electrical contact(s) to the framework, as will be discussed.

The assembled framework may comprise any suitable and desired shape. In one embodiment the framework comprises a substantially cuboid shape, e.g. assembled from a plurality of stacked rectangular layers. Preferably the framework comprises one or more depressions arranged to locate the one or more electrical contacts respectively. For example, when the molecular electronic device comprises two contacts, preferably the framework comprises depressions formed in opposite sides of the framework for locating respective contacts. The (e.g. concave) shape of the depression(s) may be used (e.g. in addition to the number of layers of the framework) to control the spacing of the molecular electronic component(s) from the contact(s) and, e.g., the spacing of the contacts from each other when the molecular electronic device comprises more than one contact.

The one or more molecular electronic components, which are connected to the framework, may be any suitable and desired molecular electronic component(s). Preferably the one or more molecular electronic components (e.g. each) have a well (e.g. precisely) defined atomic structure, e.g. as opposed to less well-defined molecular structures such as carbon nanotubes (which usually do not have a defined number of carbon atoms). Thus preferably (e.g. each of) the one or more molecular electronic components is a well-defined (e.g. discrete and preferably single) molecule or group of molecules. Preferably (e.g. each of) the one or more molecular electronic components is not a carbon nanotube.

(A well-defined molecule (or group of molecules) is one with a precisely defined formula (atomic composition) and structural formula (showing how the constituent atoms are connected by chemical bonds). For any particular well-defined molecule (or group of molecules), some or all of its stereoisomers (having the same structural formula but different spatial arrangements of atoms), may be taken as being functionally equivalent. Thus a mix of stereoisomers may be considered as being the same particular well-defined molecule (or group of molecules).)

In one embodiment the one or more molecular electronic components has a molecular mass between 100 Dalton (Da) and 10,000 Da, e.g. between 500 Da and 5,000 Da, e.g. between 1,000 Da and 3,000 Da, e.g. approximately 2,600 Da.

In one embodiment the one or more molecular electronic components comprises a magnetic heterometallic ring. In one embodiment the one or more molecular electronic components comprises an antiferromagnetic ring. Preferably the ring comprises a $Cr_7M$ ring, wherein M comprises a metal, e.g. Ni (e.g. $Ni^{II}$), Co (e.g. $Co^{II}$), Fe (e.g. $Fe^{II}$ or $Fe^{III}$).

In one embodiment the one or more molecular electronic components comprises a rotaxane. Preferably the rotaxane comprises a (macrocyclic) ring having an axle extended therethrough. Preferably the axle (e.g. having a dumbbell shape) is held within the ring. Preferably the (e.g. hybrid) rotaxane comprises an inorganic ring and an organic axle. Preferably the inorganic ring comprises a magnetic heterometallic ring and/or an antiferromagnetic ring, e.g. a $Cr_7M$ ring, wherein M comprises a (e.g. transition) metal, e.g. Ni (e.g. $Ni^{II}$), Co (e.g. $Co^{II}$), Fe (e.g. $Fe^{II}$ or $Fe^{III}$).

In these above embodiments preferably the one or more molecular electronic components is to be used as (and thus preferably comprises) a molecular quantum dot.

Such molecular electronic components, e.g. molecular nanomagnets (e.g. based on antiferromagnetically-coupled clusters of transition metals), help to provide atomically well-defined (e.g. groups of) molecules such as molecular quantum dots, e.g. having internal magnetic degrees of freedom.

Preferably the method comprises selecting a particular (e.g. well-defined) molecule or group of molecules to use as the one or more molecular components. In a preferred embodiment the method comprises (e.g. designing and) synthesising (e.g. a particular (e.g. well-defined) molecule or group of molecules to use as) the one or more molecular components. As has been explained, a (e.g. a well-defined) molecular electronic component, when connected to one or more of the plurality of polynucleotides, has the ability to align or self-assemble (and thus, e.g., accurately position) itself with respect to the framework of the molecular electronic device, owing the (e.g. well-defined) nature of the molecular electronic component (e.g. such that copies of the molecular electronic component are (substantially) identical), in a way that would not always be possible for a less well-defined structure (such as a carbon nanotube).

The one or more molecular electronic components may comprise any suitable and desired type of electronic components. For example, the one or more molecular electronic components may comprise one or more of: a diode, a (e.g. field effect) transistor, a (e.g. molecular spin) qubit or a (e.g. magnetic) molecular quantum dot, etc. . . . In one embodiment the molecular electronic component(s) comprise a single molecule electronic component. Preferably the one or more molecular electronic components are configured such that they are (e.g. each) able to be connected to the framework, e.g. via one or more covalent bonds to polynucleotides that hybridize with other components of the framework, as will be discussed below.

The molecular electronic component(s) may be connected to one or more of the plurality of polynucleotides forming the framework in any suitable and desired way. In one set of embodiments the molecular electronic device comprises one or more ("connecting") polynucleotides attached to (e.g. each of) the molecular electronic component(s) and arranged to connect the molecular electronic component(s) to the one or more of the plurality of polynucleotides forming the framework, to locate the molecular electronic component(s) with respect to the framework (and to the one or more electrical contacts).

Thus preferably the method comprises attaching one or more polynucleotides to (e.g. each of) the molecular electronic component(s), and using the one or more polynucleotides attached to the molecular electronic component(s) to locate the molecular electronic component(s) with respect to the framework, e.g. by hybridizing the polynucleotide(s) attached to the molecular electronic component(s) to one or more of the plurality of polynucleotides forming the framework.

Preferably the polynucleotide(s) that are attached to the molecular electronic component(s) are connected to the one or more of the plurality of polynucleotides forming the framework at the same time and in the same assembly process as that used to assemble the framework, e.g. by annealing or otherwise combining the plurality of polynucleotides forming the framework with the polynucleotides that are attached to the molecular electronic component(s).

In these embodiments, preferably the molecular electronic component(s) are connected to the framework via hybridization of the polynucleotide(s) attached to the molecular electronic component(s) with a single-stranded section of one or more polynucleotides that form part of the framework. Thus preferably the polynucleotide(s) attached to the molecular electronic component(s) do not themselves form part of, but instead are attached to, the framework.

In one embodiment the molecular electronic component(s) are (e.g. each) attached directly to one or more of the plurality of polynucleotides which form the framework, e.g. not via one or more additional connecting polynucleotides. Thus preferably the method comprises attaching (e.g. each of) the one or more molecular electronic components to one or more of the plurality of polynucleotides that form the framework. In the embodiment in which the framework is assembled according to the "DNA origami" technique, the molecular electronic component(s) may be attached directly to the (e.g. longer) "scaffold" polynucleotide and/or to one or more of the (e.g. shorter) polynucleotide "staples" which form the framework.

The molecular electronic component(s) may be attached to the one or more polynucleotides that are used to locate the molecular electronic component(s) with respect to the framework in any suitable and desired way. In one embodiment the molecular electronic component(s) are attached to the respective ends of one or more of the plurality of polynucleotides forming the framework or to one or more connecting polynucleotides, e.g. as a terminal modification. Thus, for example, the molecular electronic component(s) are prepared with the one or more polynucleotides attached to them in this way, e.g. for then connecting to or forming the framework.

In another embodiment the one or more molecular electronic components are attached as an internal modification to one or more of the plurality of polynucleotides forming the framework, or to the one or more connecting polynucleotides (i.e. such that the modified polynucleotide is continuous across the molecular electronic component, the ends of the polynucleotide project from either side of the molecular electronic component, and the ends are free (i.e. single-stranded), e.g. to hybridize with complementary polynucleotides).

In order to attach the molecular electronic component(s) to one or more of the plurality of polynucleotides forming the framework or to one or more connecting polynucleotides, the polynucleotide(s) may first be bound to one or more complementary polynucleotides as part of a double helix. This may help to locate and thus attach the molecular electronic component to the one or more polynucleotides (e.g. via one or more respective covalent bonds). Once the molecular electronic component has been attached to the one or more polynucleotides, preferably the complementary polynucleotide is removed, leaving the molecular electronic component attached to the one or more polynucleotides forming the framework or to the one or more connecting polynucleotides.

In one embodiment the molecular electronic component(s) are (e.g. each) inserted, for example, as a backbone link in one or more of the plurality of polynucleotides forming the framework or in the one or more connecting polynucleotides.

In one set of embodiments the plurality of polynucleotides forming the framework, the molecular electronic component(s) (and, where appropriate, the one or more connecting polynucleotides) may be arranged such that the framework is only able to assemble (e.g. correctly) when the molecular electronic component(s) are present. Thus the plurality of polynucleotides may be prevented from assembling (e.g. correctly) into the framework when the molecular electronic component(s) and their attached polynucleotides are not present. This may help to exert tighter control over the assembly of the framework and/or the positioning of the molecular electronic component(s).

The molecular electronic component(s) may (e.g. each) be attached to the one or more of the plurality of polynucleotides or to the one or more connecting polynucleotides (for connecting to the framework) in any suitable and desired way. In one embodiment the molecular electronic component(s) are (e.g. each) attached to the one or more of the plurality of polynucleotides forming the framework or to the one or more connecting polynucleotides via one or more respective covalent bonds.

Preferably (e.g. each of) the one or more of the plurality of polynucleotides forming the framework or the one or more connecting polynucleotides to which the molecular electronic component(s) are attached comprises a peripheral functional group (e.g. a thiol, carboxyl, amine, alkyne, azide or acrydite) to form the covalent bond(s) with the molecular electronic component(s). Thus preferably the method comprises functionalising one, more or all of the molecular electronic component(s) and the one or more of the plurality of polynucleotides forming the framework and/or the one or more connecting polynucleotides for attaching to each other, as appropriate.

While, in some embodiments, the molecular electronic component(s) may (e.g. each) be connected to the framework using or via only a single framework polynucleotide or connecting polynucleotide, it will be appreciated that in some embodiments, connecting the molecular electronic component(s) to the framework (e.g. each) using two or three (or more) polynucleotides forming the framework or connecting polynucleotides (e.g. per molecular electronic component), may help to locate (and, e.g., orient) the molecular electronic component(s) with respect to the framework more accurately and/or help to strengthen or stiffen the connection(s) of the molecular electronic component(s) to the framework.

It will be appreciated when multiple polynucleotides forming the framework or connecting polynucleotides are attached to (e.g. each of) the molecular electronic component(s) for connecting and locating the molecular electronic component(s) to the framework, they may be attached in multiple different ways, e.g. using one or more of the techniques outlined herein.

The molecular electronic component(s) may (e.g. each) be located with respect to the framework in any suitable and desired position(s), e.g. independently of how the molecular electronic component(s) are connected to the polynucleotides forming the framework. In one embodiment the molecular electronic component(s) are located substantially at the centre of the framework. When the framework comprises a depression (e.g. for locating the contact(s)), preferably the molecular electronic component(s) are located substantially at the centre (e.g. the base) of the depression.

The one or more electrical contacts of the molecular electronic device that are located with respect to the framework and to the one or more molecular electronic components, and which form a coupling to the one or more molecular electronic components, may be any suitable and desired type of electrical contacts. Preferably the contact(s) (once located on the framework) are (each) arranged to be connected to a contact or docking site. This is in order to allow an electrical connection to be made with external circuit components (e.g. via a contact pad to components on a (e.g. lithographically) patterned surface) or to a contact in another molecular electronic device. Thus preferably the method comprises connecting each of the one or more contacts to a contact pad (e.g. of an external circuit) or a contact of another molecular electronic device.

In one embodiment the one or more electrical contacts are extrinsically fabricated, i.e. the one or more electrical contacts are fabricated before being connected to one or more of the plurality of polynucleotides for coupling to the one or more molecular electronic components. Thus preferably the method comprises fabricating the one or more electrical contacts (e.g. at the size outlined below) and then connecting the one or more fabricated electrical contacts to one or more of the plurality of polynucleotides. Preferably the one or more electrical contacts are each fabricated as single particles, e.g. contrasting with the use of multiple seed (e.g. nano) particles to nucleate the growth of a contact in situ.

In one embodiment the one or more electrical contacts comprise one or more inorganic contacts (i.e. contact(s) formed from an inorganic material), e.g. one or more metal contacts. In one embodiment the one or more electrical contacts comprise one or more gold contacts. In one embodiment the one or more electrical contacts comprise one or more conducting nanoparticles.

In one embodiment the one or more electrical contacts comprise one or more conducting molecular components, e.g. one or more conducting oligomers. These one or more conducting molecular components preferably comprise functional groups to contact to a contact pad (e.g. of an external circuit) or a contact of another molecular electronic device.

Preferably the one or more electrical contacts (each) have a maximum dimension (e.g. diameter) of between 20 nm and 100 nm, e.g. between 40 nm and 80 nm, e.g. between 50 nm and 70 nm, e.g. approximately 60 nm. Preferably the one or more electrical contacts (each) have a minimum dimension greater than 10 nm, e.g. greater than 30 nm, e.g. greater than 50 nm. Thus preferably the one or more electrical contacts comprise one or more gold nanoparticles, e.g. having a diameter of approximately 60 nm. Providing electrical contact(s) of this size helps them to be connected to external electrical connection(s), e.g. using lithographic techniques to connect, for example, to a contact pad on a (e.g. lithographically) patterned surface or to another contact in another molecular electronic device.

Preferably the one or more electrical contacts are (each) larger than the one or more molecular electronic components of the device. This is because the external electrical connection(s) that may be required to wire up the electrical contact(s) are typically formed explicitly using fabrication techniques such as lithography. This contrasts with the coupling between the electrical contact(s) and the molecular electronic component(s) which is preferably formed automatically owing to the connections between the plurality of polynucleotides and each of the electrical contact(s) and the molecular electronic component(s).

The one or more electrical contacts may be connected to one or more of the plurality of polynucleotides forming the framework in any suitable and desired way. In one set of embodiments the molecular electronic device comprises one or more connecting polynucleotides attached to (e.g. each of) the electrical contact(s) and arranged to connect the electrical contact(s) to the one or more of the plurality of polynucleotides forming the framework, to locate the electrical contact(s) with respect to the framework (and to the one or molecular electronic components).

Thus preferably the method comprises attaching one or more connecting polynucleotides to (e.g. each of) the electrical contact(s), and connecting the electrical contact(s) to the one or more of the plurality of polynucleotides forming the framework to locate the electrical contact(s) with respect to the framework using the one or more connecting polynucleotides attached to the electrical contact(s). In one embodiment, e.g. as with the extrinsic fabrication of the electrical contact(s), preferably the one or more connecting polynucleotides are attached to the one or more electrical contact(s) extrinsically, before the one or more contacts are connected to the one or more of the plurality of polynucleotides. This contrasts with the use of a chemical group that is used to attract or nucleate a seed particle for further aggregation or deposition to form a contact.

In these embodiments, preferably the electrical contact(s) are connected to the framework via hybridization of the connecting polynucleotide(s) attached to the electrical contact(s) with the single-stranded section (e.g. sticky end) of one or more polynucleotides that form part of the framework. Thus preferably the connecting polynucleotide(s) attached to the electrical contact(s) do not themselves form part of, but instead are attached to, the framework.

In one embodiment the electrical contact(s) are (e.g. each) attached directly to one or more of the plurality of polynucleotides which form the framework, e.g. not via one or more additional connecting polynucleotides. Thus preferably the method comprises attaching (e.g. each of) the one or more electrical contacts to one or more of the plurality of polynucleotides forming the framework. In the embodiment in which the framework is assembled according to the "DNA origami" technique, the electrical contact(s) may be attached directly to the (e.g. longer) "scaffold" polynucleotide and/or to one or more of the (e.g. shorter) polynucleotide "staples" which form the framework.

For example, the framework may comprise one or more docking sites for the one or more electrical contacts respectively. The electrical contact(s) may be located at the docking site(s) via non-specific attractive interactions (e.g. van der Waals forces). Thus preferably one or more of the plurality of polynucleotides which form the framework are prepared with non-specific attractive interactions to form the docking site(s).

In the embodiments outlined above, e.g. in which the electrical contact(s) are attached to one or more of the polynucleotides that form the framework or to one or more connecting polynucleotides, the electrical contact(s) may be attached to these polynucleotides in any suitable and desired way, e.g. via the docking site(s). The electrical contact(s) may be attached to the polynucleotide(s) or connecting polynucleotide(s) before or after these polynucleotide(s) are assembled to form the framework or attached to the framework, or the electrical contact(s) may be attached during the assembly of the polynucleotide framework.

In one embodiment the electrical contact(s) are attached to the respective ends of one or more of the plurality of polynucleotides forming the framework or to the one or more connecting polynucleotides. Thus, for example, the electrical contact(s) may be prepared with the one or more polynucleotides attached to them in this way, e.g. for then connecting to or forming the framework.

While, in some embodiments, the one or more electrical contacts may (e.g. each) be connected to the framework using or via only a single polynucleotide or connecting polynucleotide, it will be appreciated that in some embodiments, connecting the one or more electrical contacts to the framework (e.g. each) using two or three (or more) polynucleotides forming the framework or connecting polynucleotides (e.g. per electrical contact), may help to locate the one or more electrical contacts with respect to the framework more accurately and/or help to strengthen or stiffen the connection of the one or more electrical contacts to the framework. This may help to provide a reliable electrical connection between the one or more electrical contacts and the one or more molecular electronic components.

In a preferred embodiment the molecular electronic device comprises between 1 and 10,000 connecting polynucleotides (e.g. approximately 1,000 connecting polynucleotides) attached to (e.g. each of) the one or more electrical contacts for connecting the one or more electrical contacts to one or more of the plurality of polynucleotides forming the framework, so as to form a coupling between the one or more electrical contacts and the one or more molecular electronic components (and, e.g., between multiple (e.g. pairs of) molecular electronic components). Preferably the plurality of polynucleotides forming the framework comprise between 1 and 100 (e.g. approximately 10) polynucleotides (e.g. per electrical contact) each comprising a single-stranded section (e.g. sticky end) for hybridizing with complementary polynucleotides attached to the one or more electrical contacts so as to connect the one or more electrical contacts to the plurality of polynucleotides forming the framework.

In one embodiment the framework comprises two or more locations for locating two or more electrical contacts respectively, wherein the one or more polynucleotides forming the framework at each of the two or more locations have different (e.g. combinations of) base sequences (e.g. in their single-stranded section). This may help to direct differently sized electrical contacts to different locations on the framework. However, it will be appreciated that multiple electrical contacts may be connected to the polynucleotides forming the framework using the same base sequence.

It will be appreciated when multiple polynucleotides or connecting polynucleotides are attached to (e.g. each of) the molecular electronic component(s) for connecting and locating the molecular electronic component(s) to the framework, they may be attached in multiple different ways, e.g. using one or more of the techniques outlined herein.

The one or more electrical contacts may (e.g. each) be attached to the one or more of the plurality of polynucleotides forming the framework or to the one or more connecting polynucleotides (for connecting to the framework) in any suitable and desired way. In one embodiment the one or more electrical contacts are (e.g. each) attached to the one or more of the plurality of polynucleotides forming the framework or to the one or more connecting polynucleotides via respective covalent bonds.

Preferably (e.g. each of) the one or more of the plurality of polynucleotides forming the framework or the one or more connecting polynucleotides to which the molecular electronic component(s) are attached comprises a peripheral functional group (e.g. a thiol, carboxyl, amine, alkyne, azide or acrydite) to form the covalent bond(s) with the respective electrical contact(s). In one embodiment, thiol or heterocyclic carbene functionalities may be used to form bonds directly with a gold surface. Thus preferably the method comprises functionalising one, more or all of the electrical contact(s) and/or the one or more of the plurality of polynucleotides forming the framework and/or the one or more connecting polynucleotides for attaching to each other, as appropriate.

When the one or more electrical contacts are located with respect to the framework, this forms a coupling (or couplings) between (e.g. each of) the one or more electrical contacts and the one or more molecular electronic components. The coupling(s) allow the molecular electronic device to be incorporated into a larger circuit, such that operation of the molecular electronic component(s) may be controlled via the electrical contact(s), e.g. by applying an electrical potential.

The coupling between (e.g. each of) the one or more electrical contacts and the one or more molecular electronic components (and, e.g., between multiple (e.g. pairs of) molecular electronic components) may be any suitable and desired coupling, e.g. which allows the operation of the molecular electronic component(s) to be controlled. In one embodiment the coupling comprises a (e.g. highly electrically) conductive coupling (e.g. an electron-transparent high-conductance coupling). In another embodiment the coupling comprises a (e.g. highly electrically) resistive coupling (e.g. an electron-opaque high-resistance coupling). It will be appreciated that when the molecular electronic device comprises a plurality of couplings, between the one or more molecular electronic components and a plurality of electrical contacts (and, e.g., between multiple (e.g. pairs of) molecular electronic components), the plurality of couplings may comprise any suitable and desired mix of conductive and non-conductive couplings.

The type of coupling may depend on the type of molecular electronic component and how it is desired to be controlled. For example, when the molecular electronic component comprises a field effect transistor, the couplings to the source and drain terminals each comprise a conductive coupling and the coupling to the gate terminal comprises a non-conductive coupling (but, e.g., the gate is close enough to the channel of the transistor to influence conduction between the source and drain terminals).

The coupling(s) may be formed in any suitable and desired way. In one embodiment the coupling(s) may be (e.g. each) formed by controlling the distance(s) between the locations of the electrical contact(s) and the molecular electronic component(s) (and, e.g., between multiple (e.g. pairs of) molecular electronic components) on the framework, e.g. owing to the design (e.g. shape and/or size) of the framework. For example, the number of layers of the framework and/or the shape and/or size of the depression on the framework in which the electrical contact(s) are located may be chosen to control the distance(s) between the electrical contact(s) and the molecular electronic component(s).

Such a (e.g. electrostatic) coupling formed by virtue of the distance may be a conductive coupling (e.g. a tunnelling connection) or a non-conductive coupling. Thus, in one embodiment the coupling allows the tunnelling of electrons across the coupling. The conductive or non-conductive nature of the coupling(s) may be controlled by the distance between the molecular electronic component(s) and the electrical contact(s) (or between multiple (e.g. pairs of) molecular electronic components) that are coupled together by the coupling, which in turn is preferably set by the relative positions of the molecular electronic component(s) and the electrical contact(s) on the framework.

In one embodiment the coupling is formed only by controlling the distance between the respective molecular electronic component(s) and the electrical contact(s) (or between multiple (e.g. pairs of) molecular electronic components) and, e.g., does not comprise a chemical bond therebetween. Preferably such a coupling is non-conductive (high impedance).

In one embodiment the coupling is formed through the formation of a covalent or other chemical bond between the one or more molecular electronic components and the one or more electrical contacts.

In one embodiment some or all of the molecular electronic component(s) and the electrical contact(s) are functionalised to form the coupling(s) when the molecular electronic component(s) and the electrical contact(s) are located on the framework and with respect to each other. Thus preferably the method comprising functionalising some or all of the molecular electronic component(s) and the (e.g. respective) electrical contact(s), such that the coupling(s) are formed when the molecular electronic component(s) and/or the electrical contact(s) are located on the framework and with respect to each other. Providing a chemical functionality on the molecular electronic component(s) and/or the electrical contact(s) helps to allow the formation of a bond between the molecular electronic component(s) and the (e.g. respective) electrical contact(s) (or between multiple (e.g. pairs of) molecular electronic components), such that the properties of the bond determines the (e.g. conductive or non-conductive) nature of the coupling.

It will be appreciated that in some embodiments the formation of the coupling(s) is controlled through a combination of the distance between the molecular electronic component(s) and the (e.g. respective) electrical contact(s) (or between multiple (e.g. pairs of) molecular electronic components), and the chemical functionality of the molecular electronic component(s) and/or the (e.g. respective) electrical contact(s). For example, the relative location(s) of the molecular electronic component(s) and the (e.g. respective) electrical contact(s) (or the (e.g. pairs of) molecular electronic components) on the framework may be chosen such that the distance between them dictates the type of chemical bond(s) which are formed to provide the coupling(s). This helps to give precise control of the relative positions and spacing of the molecular electronic component(s) and the (e.g. respective) electrical contact(s) (or the (e.g. pairs of) molecular electronic components), while providing the desired (e.g. conductive or non-conductive) coupling therebetween.

When the coupling is formed by virtue of a chemical functionality on the molecular electronic component(s) and/or the (e.g. respective) electrical contact(s) (or the (e.g. pairs of) molecular electronic components), the coupling may be a conductive coupling or a non-conductive coupling. The conductive or non-conductive nature of the coupling(s) may be controlled by the chemical structure of the bond between the molecular electronic component(s) and the (e.g. respective) electrical contact(s) (or between multiple (e.g. pairs of) molecular electronic components) that are coupled together by the coupling and/or by the chemical structure of the proximal part (e.g. surface) of the molecular electronic component(s) and/or the (e.g. respective) electrical contact(s) (or the proximal part(s) of the (e.g. pairs of) molecular electronic component(s)). For example, the chemical bond may be conductive or non-conductive, and/or the proximal part (e.g. surface or proximal chemical bonds) of the molecular electronic component(s) and/or the (e.g. respective) electrical contact(s) (or the proximal part(s) of the (e.g. pairs of) molecular electronic component(s)) may be conductive or non-conductive (insulating), as appropriate to form the desired coupling.

In one set of embodiments, the molecular electronic device comprises one or more conducting oligomers or other substantially electrically conducting molecules arranged between the molecular electronic component(s) and (e.g. each of) the one or more electrical contacts (or between multiple (e.g. pairs of) molecular electronic components) to form part of the coupling between the molecular electronic component(s) and the electrical contact(s) (or between multiple (e.g. pairs of) molecular electronic components). Thus preferably the method comprises attaching one or more conducting oligomers or other substantially electrically conducting molecules between the molecular electronic component(s) and (e.g. each of) the electrical contact(s) (or between multiple (e.g. pairs of) molecular electronic components).

Preferably the one or more conducting oligomers or other substantially electrically conducting molecules are attached (e.g. at each of their respective ends) to the molecular electronic component(s) and to the electrical contact(s), e.g. via a covalent bond. The one or more conducting oligomers or other substantially electrically conducting molecules may be attached to the molecular electronic component(s) and/or the electrical contact(s) before or after the molecular electronic component(s) and/or the electrical contact(s) are connected to the framework, or the one or more conducting oligomers or other substantially electrically conducting molecules may be attached during one of the same assembly steps outlined above, e.g. of assembling the polynucleotide framework.

Any of the techniques outlined above for locating molecular electronic components or electrical contacts with respect to the polynucleotide framework and to each other may be used to locate the conducting oligomers or other substantially electrically conducting molecules with respect to the framework and to the other components of the device by means of one or more polynucleotides attached to (e.g. each) conducting oligomer or other substantially electrically conducting molecule. In one embodiment the coupling between the one or more conducting oligomers or other substantially electrically conducting molecules and the one or more molecular electronic components and/or the one or more electrical contacts (e.g. forming part of the coupling between the one or more molecular electronic components and the one or more electrical contacts) is formed by controlling the distance between the one or more conducting oligomers or other substantially electrically conducting molecules and the one or more molecular electronic components and/or the one or more electrical contacts.

Thus, in a similar manner as outlined above for the molecular electronic component(s) and/or the electrical contact(s), in one embodiment the one or more conducting oligomers or other substantially electrically conducting molecules are functionalised to attach them to the respective molecular electronic component(s) and electrical contact(s) to form the coupling(s). Thus preferably the method comprises functionalising one, more or all of the molecular electronic component(s), the electrical contact(s) and the one or more conducting oligomers or other substantially electrically conducting molecules for attaching to each other, as appropriate. Again, preferably the chemical nature of the one or more conducting oligomers or other substantially electrically conducting molecules, their functionality and/or their attachment to the respective molecular electronic component(s) and electrical contact(s) is configured to determine the (e.g. conductive or non-conductive) nature of the coupling(s).

When the various parts of the device are functionalised to attach themselves to each other, preferably one or both of the molecular electronic component(s) and the electrical contact(s) comprise one or more functional groups (e.g. a thiol, carboxyl, amine, alkyne, azide or acrydite). As outlined above, the chemical functionality helps to allow the formation of a (e.g. covalent) bond between the parts of the device that are being attached to each other. For example, a thiol or heterocyclic carbene functionality on a molecular electronic component may react with the (e.g. gold) surface of the electrical contact to provide a (e.g. —S—Au) bond.

The molecular electronic device may be assembled in any suitable and desired way. In one embodiment one or more (e.g. all) of the assembly steps (e.g. of assembling the framework from the plurality of polynucleotides, connecting the molecular electronic component(s) to the framework, connecting the electrical contact(s) to the framework, coupling the molecular electronic component(s) to each other and to the electrical contact(s)) are performed in an aqueous solution (e.g. a buffer solution providing a suitable pH), e.g. during the same or separate annealing processes. In another embodiment one or more of these assembly steps are performed in an alternative solvent such as glycerol and choline chloride, or a mixture of solvents such as dimethylformamide and water.

Preferably a plurality of molecular electronic devices are assembled simultaneously, e.g. by combining the necessary constituent parts together and, e.g., annealing the framework and the other constituent parts. It will be appreciated that the chemical nature of the assembly of the molecular electronic device facilitates the mass production of such devices in an efficient and repeatable way, while maintaining the accuracy of assembling each individual device, such that many (e.g. trillions of) substantially identical molecular electronic devices may be made at the same time.

Thus when viewed from a further aspect the invention provides a method of assembling a plurality of (e.g. substantially identical) molecular electronic devices, the method comprising:

assembling a plurality of frameworks, each framework assembled from a plurality of polynucleotides;
wherein for each of the plurality of frameworks the method comprises:
connecting one or more molecular electronic components to one or more of the plurality of polynucleotides; and
connecting one or more electrical contacts to one or more of the plurality of polynucleotides;
wherein the one or more molecular electronic components and the one or more electrical contacts are each connected to one or more of the plurality of polynucleotides such that the one or more molecular electronic components and the one or more electrical contacts are located with respect to the framework and with respect to each other so as to form a coupling between the one or more electrical contacts and the one or more molecular electronic components.

When viewed from a further aspect the invention provides a plurality of molecular electronic devices obtainable by a method as outlined in the above aspect of the invention.

It will be appreciated that the above aspects may (and preferably do) comprise any one or more (e.g. all) of the optional and preferred features outlined herein, as appropriate. In particular, the features outlined herein referring to a single molecular electronic device and the assembly thereof preferably apply also to (e.g. each of the molecular electronic devices in the) plurality of molecular electronic devices.

Owing to the precise assembly of the polynucleotides with respect to each other, thus forming the framework and locating the one or more molecular electronic components and the one or more electrical contacts with respect to each other and to the framework, the process of the present invention may be highly repeatable and produce devices according to the present invention with a high yield. In one embodiment the method produces greater than $10^9$, e.g. greater than $10^{10}$, e.g. greater than $10^{11}$, e.g. approximately $10^{12}$ (e.g. substantially identical) molecular electronic devices in a single reaction. In one embodiment the method has a yield (the percentage of the sets of constituent parts that have been assembled (e.g. correctly) into the (e.g. substantially identical) molecular electronic devices) of greater than 10%, e.g. greater than 20%, e.g. greater than 30%, e.g. greater than 40%, e.g. greater than 50%, e.g. greater than 60%, e.g. greater than 70%, e.g. greater than 80%, e.g. greater than 90%.

Thus when a plurality of molecular electronic devices are assembled together, preferably at least 50%, at least 60%, at least 70%, at least 80%, e.g. at least 90% of the plurality of the one or more molecular electronic components are substantially identical. Preferably at least 50%, at least 60%, at least 70%, at least 80%, e.g. at least 90% of the plurality of the one or more electrical contacts are substantially identical. Preferably at least 50%, at least 60%, at least 70%, at least 80%, e.g. at least 90% of the plurality of the frameworks are substantially identical.

It will be appreciated that the capability of the molecular electronic devices to align or self-assemble themselves (e.g. owing to the well-defined (and, e.g., substantially identical) nature of the molecular electronic components), helps to provide a process that is reproducible with a high yield. Such molecular systems compare favourably in this regard to the heterogeneous nature of carbon nanotubes, metallic nanodots and semiconductor quantum dots, the assembly of which is likely to result in a lower yield.

Once the molecular electronic device has been assembled, preferably the molecular electronic device (e.g. a plurality of molecular electronic components and electrical contacts assembled together) is deposited on a (e.g. insulating) substrate. Thus preferably the molecular electronic device comprises a substrate on which the framework (and the molecular electronic component(s), the electrical contact(s) and any other relevant constituent parts, e.g. the coupling(s)) is deposited.

The substrate may be any suitable and desired substrate. In one embodiment the substrate comprises a (e.g. silicon dioxide on) silicon substrate. It will be appreciated that the nature of the molecular electronic device and, in particular, the framework, may help to allow it to be arranged on such a substrate.

Once the molecular electronic device has been deposited on the substrate, e.g. such that the relative positions of the molecular electronic component(s), the electrical contact(s) and any other relevant constituent parts, e.g. the coupling(s), have been fixed, all or part of the framework may be dissolved, leaving the remaining parts of the molecular electronic device attached to the substrate. Thus, in one embodiment, the method comprises dissolving at least part of the framework.

The polynucleotides forming the framework may be removed or dissolved using enzymatic or chemical degradation. Use of RNA as the polynucleotides forming the framework may be particularly suitable for this purpose, owing to RNA being less chemically stable than DNA.

In one embodiment the substrate comprises a pre-patterned substrate. This may help to locate and orient the molecular electronic device(s) deposited on the substrate and/or to make external electrical connections to the one or more contacts of the molecular electronic device. Preferably the pre-patterned substrate comprises one or more contact pads, e.g. for connecting external wires to the contact pads and/or for connecting to the one or more contacts of the molecular electronic device.

Preferably electrical connections (i.e. external to the molecular electronic device) are made to the one or more electrical contacts, e.g. from contact pad(s) on the substrate. Thus preferably the method comprises forming one or more electrical connections from the one or more electrical contacts, e.g. to one or more contact pads on a (e.g. lithographically) patterned surface or to one or more other contacts in one or more molecular electronic devices. In one embodiment lithography, e.g. electron beam-induced deposition (e.g. of platinum) or the patterned deposition (e.g. of gold) by means of resist processing, is used to form the electrical connections (e.g. wires on the substrate) to the one or more electrical contacts.

Thus preferably the molecular electronic device comprises one or more electrical connections to the one or more electrical contacts respectively. Preferably the one or more electrical connections are formed to (e.g. external) electronic circuitry or to other molecular electronic device(s). Thus plural molecular electronic devices may be connected (e.g. directly) together by electrical connection(s) being formed between their respective contacts.

In another embodiment, e.g. if the device is located accurately enough, direct contact is made between the one or more electrical contacts and one or more respective contact pads on the substrate. Thus, plural molecular electronic devices may be connected (e.g. directly) together by direct connections between the respective contacts of the molecular electronic devices, e.g. owing to their relative positioning (e.g. on a substrate) or to the hierarchical assembly of multiple devices through hybridization of polynucleotides, and without the need for the formation of additional electrical connections. This may avoid the need to form any intermediate electrical connections.

It will be appreciated that the molecular electronic device may comprise a plurality of molecular electronic components each connected to one or more of the plurality of polynucleotides that form the framework. In these embodiments, one or more (or all) of the techniques outlined above may be used to connect the various constituent parts of the molecular electronic device together such that the molecular electronic components and the electrical contact(s), as well as the connecting oligomer(s) and coupling(s), where necessary, are connected to and located with respect to the framework such that couplings between the molecular electronic components and the electrical contact(s) are formed.

Thus, in some of the embodiments, multiple molecular electronic components may be connected to the framework and coupled to respective electrical contact(s). However, preferably the multiple molecular electronic components are coupled to each other as well as to one or more electrical contacts. This allows multiple molecular electronic components to be wired up as part of a more complex circuit rather than just having a single molecular electronic component located on each framework.

One or more (e.g. all) of the connections, couplings, attachments, etc., for a molecular electronic device comprising a plurality of molecular components may be provided as outlined in any of the embodiments described herein. For example, the methods described above to form the coupling(s) between a molecular electronic component and a respective electrical contact may apply equally to form (e.g. conductive or non-conductive) coupling(s) between two or more molecular electronic components which are located with respect to each other on the framework in the same manner as a molecular electronic component and a respective electrical contact. In this way, a molecular integrated circuit may be formed having inputs and outputs coupled to respective electrical contacts.

Thus, it will be appreciated that plural molecular electronic devices according to the present invention may be assembled together to form larger composite devices, e.g. in a hierarchical assembly scheme using techniques of molecular self-assembly, with (e.g. internal) connections formed between the contacts on the component molecular electronic devices.

Various embodiments of the present invention will now be described by way of example only and with reference to the accompanying drawings, in which.

Molecular electronic components may be able to provide the ultimate limit for miniaturising electrical circuits. At this scale, quantum phenomena dominate the properties of such devices and so molecular electronic components may be able to be used to investigate the development of components for quantum technologies. Embodiments of the present invention will now be discussed outlining a molecular electronic device and a method assembling a molecular electronic device.

Figure 1A:
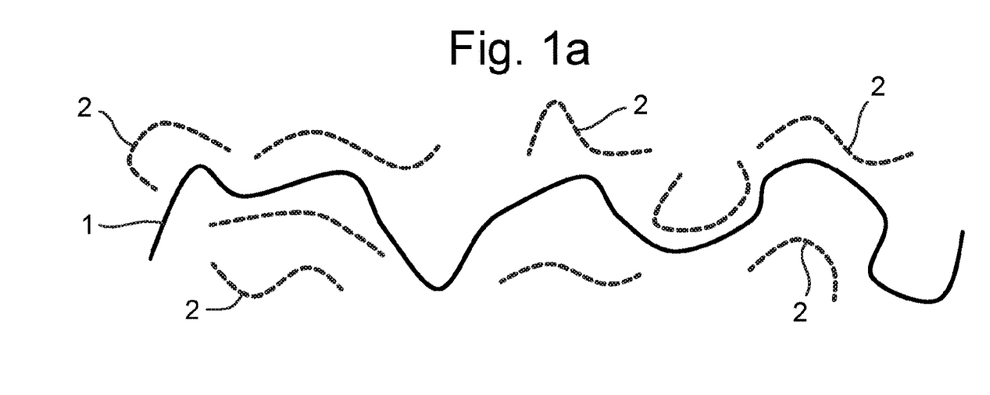
FIGS. 1a, 1b, 1c and 1d show schematically the components and structure of a molecular electronic device assembled according to an embodiment of the present invention.

FIGS. 1a, 1b, 1c and 1d show schematically a molecular electronic device 10 assembled according to an embodiment of the present invention. FIG. 1a shows schematically a single stranded DNA "scaffold" 1 and multiple "staple" polynucleotides 2. The single stranded DNA scaffold 1 is long compared to the hundreds of short polynucleotides 2 which are used to connect together parts of the single stranded DNA scaffold 1 to form a DNA framework having a maximum dimension of approximately 100 nm.

The single stranded DNA scaffold 1 may be a natural genomic sequence and the polynucleotides 2 are synthesised into a uniquely identifiable base sequence, complementary to the sequences of different sections of the DNA scaffold 1. This sequence is such that when the single stranded DNA scaffold 1 and the polynucleotides 2 are combined in a suitable aqueous buffer and annealed, the complementary bases on the DNA scaffold 1 and the polynucleotides 2 hybridize into a double stranded polynucleotide.

This process forces the DNA scaffold 1 into a precisely defined fold, held together by the polynucleotides 2 which "staple" together non-adjacent parts of the single stranded DNA scaffold 1. In this way, the single stranded DNA scaffold 1 and the polynucleotides 2 self-assemble into a DNA framework 3 formed from a double stranded polynucleotide as shown in FIGS. 1b, 1c and 1d.

Figure 1B:
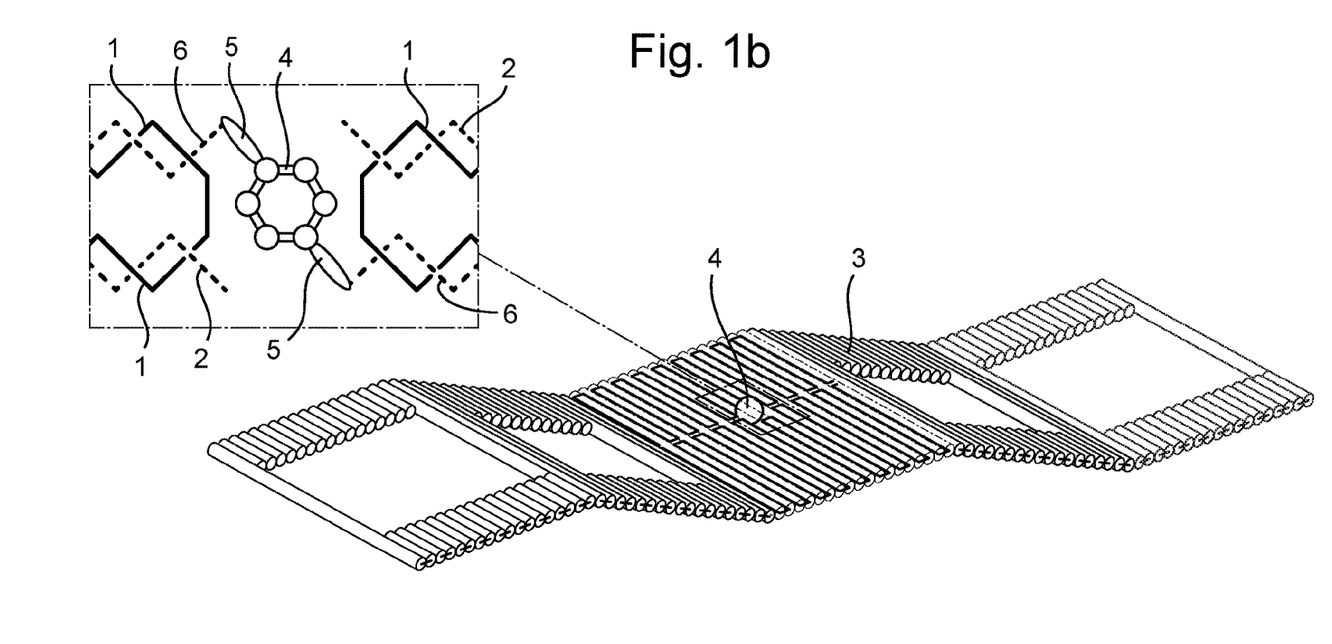
Figure 1C:
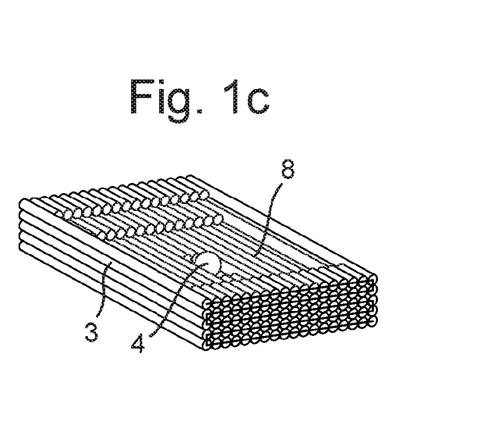
Figure 1D:
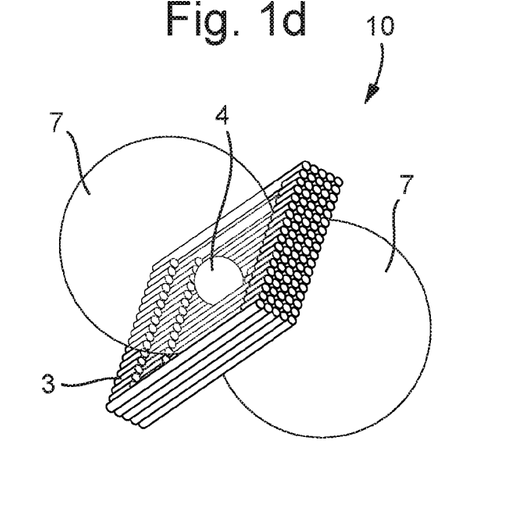

As shown schematically in FIGS. 1b and 1n FIG. 1c, the double stranded polynucleotide DNA framework 3 comprises many DNA helices arranged in parallel layers to form a three-dimensional double stranded polynucleotide structure (FIG. 1c shows it in its fully assembled form). This is achieved by polynucleotides 2 hybridizing with parts of the single stranded DNA scaffold 1 to staple the different parts together into the fully assembled DNA framework 3 shown in FIG. 1c. (It will be appreciated that the DNA framework 3 does not in general anneal into its final form shown in FIG. 1c via the intermediate form shown in FIG. 1b, which is provided more for the purposes of clarity to show the different layers of the DNA framework 3.)

Also shown in FIGS. 1b and 1c is a molecular electronic component 4 which is attached to the centre of the DNA framework 3. The molecular electronic component 4 (e.g. a molecular quantum dot formed from an artificial molecular nanomagnet, e.g. a {$Cr_7M$} ring, e.g. a hybrid rotaxane comprising a $Cr_7M$ ring) is formed and thiol-modified conducting oligomers 5 are attached via covalent bonds to the molecular electronic component 4. These conducting oligomers are to be used for coupling the molecular electronic component 4 to the gold nanoparticles which are used for wiring up the molecular electronic device externally, as will be described below. Two connecting polynucleotides 6 are attached via covalent bonds to the conducting oligomers 5.

The connecting polynucleotides 6 are synthesised with uniquely identifiable base sequences for hybridizing with complementary bases on the single stranded DNA scaffold 1 as part of the DNA framework 3. The molecular electronic components 4, each prepared with the connecting polynucleotides 6 and conducting oligomers 5, are purified by polyacrylamide gel electrophoresis or reverse phase chromatography.

Each connecting polynucleotide 6 attached through the conducting oligomers 5 to the molecular electronic component 4 has only one possible hybridization site on the DNA framework 3 (i.e. with the complementary section of the scaffold 1), which locates the molecular electronic component 4 accurately with respect to the DNA framework 3.

The molecular electronic component 4 is connected to the DNA framework 3 by combining the molecular electronic component 4, prepared with its conducting oligomers 5 and connecting polynucleotides 6, with the single stranded DNA scaffold 1 and the "staple" polynucleotides 2. Thus, as the DNA framework 3 is annealed, the molecular electronic component 4 is located in position at the centre of the DNA framework 3.

(It should be noted that the thiol-modified conducting oligomers 5 do not necessarily have to be attached to the molecular electronic component 4 before the molecular electronic component 4 is connected to the DNA framework 3. For example, the conducting oligomers 5 and the molecular electronic component 4 could separately be provided with connecting polynucleotides 6 and thus positioned within the framework 3 such that the connections between them are formed after assembly of the framework. In another embodiment, the molecular electronic component 4 is functionalized (e.g. with thiol groups) to make direct connections to the electrical contacts without the need for the addition of intermediate conducting oligomers.)

Multiple DNA frameworks 3 each containing a molecular electronic component 4 and having a total molecular weight of typically 5 MDa, which can be assembled simultaneously by annealing all the constituent parts, are purified from excess staple polynucleotides (having a total molecular weight of typically 10 kDa) using agarose gel purification, size exclusion chromatography or polyethylene glycol precipitation.

Once the fully formed DNA framework 3 with the located molecular electronic component 4 has been assembled, as shown in FIG. 1c, gold nanoparticles 7 (having a dimension of approximately 60 nm) are located with respect to the DNA framework 3 so as to make tunnelling electrical contact with the molecular electronic component 4, as shown in FIG. 1d, via the conducting oligomers attached to the molecular electronic component 4. It can be seen from FIG. 1c that the fully formed DNA framework 3 is shaped with a depression 8 in either side for locating the gold nanoparticles 7.

The gold nanoparticles 7 are functionalised by attaching approximately 1000 thiol-modified polynucleotides via covalent bonds to each of the gold nanoparticles 7, which are then purified by filtration. Some of the polynucleotides 2 that are incorporated in the framework 3 in the vicinity of the depression 8 are synthesized with an additional overhanging base sequence for hybridizing with complementary bases on the thiol-modified polynucleotides that are attached to the gold nanoparticles 7.

This gives these polynucleotides sticky ends for hybridizing with the thiol-modified polynucleotides on the gold nanoparticles 7 to connect the gold nanoparticles 7 to the DNA framework 3. Approximately 30 polynucleotides for each gold nanoparticle 7 to be connected are attached to (e.g. form part of) the DNA framework 3. If the molecular electronic device is desired to have differently sized gold nanoparticles 7, for example, these can be directed to different sites by different binding sequences on the thiol-modified polynucleotides attached to the gold nanoparticles 7 and the complementary polynucleotides having sticky ends on the DNA framework 3.

The functionalised gold nanoparticles 7 are introduced after the fully formed DNA frameworks 3 have been annealed (although in some embodiments they may be introduced with all the other constituents parts before the DNA frameworks 3 are annealed), to dock the gold nanoparticles 7 in the depressions 8 on either side of the DNA framework 3. The connection between the polynucleotides on the gold nanoparticles 7 and the complementary sticky ends of the polynucleotides on the DNA framework 3 position the gold nanoparticles 7 with respect to the DNA framework 3 and thus to the molecular electronic component 4 such that the gold nanoparticles 7 making a tunnelling electrical connection with the conducting oligomers attached to the molecular electronic component 4, via the thiol-modified peripheral groups on the conducting oligomers which bond covalently to the gold nanoparticles 7. This electrically connects the gold nanoparticles 7 with the molecular electronic component 4 to form the completed molecular electronic device 10, as shown in FIG. 1d.

In order to connect up the assembled molecular electronic device 10 (as shown in FIG. 1d) as part of a larger (e.g. integrated) circuit, electrical connections need to be made to the gold nanoparticles 7.

Figure 2:
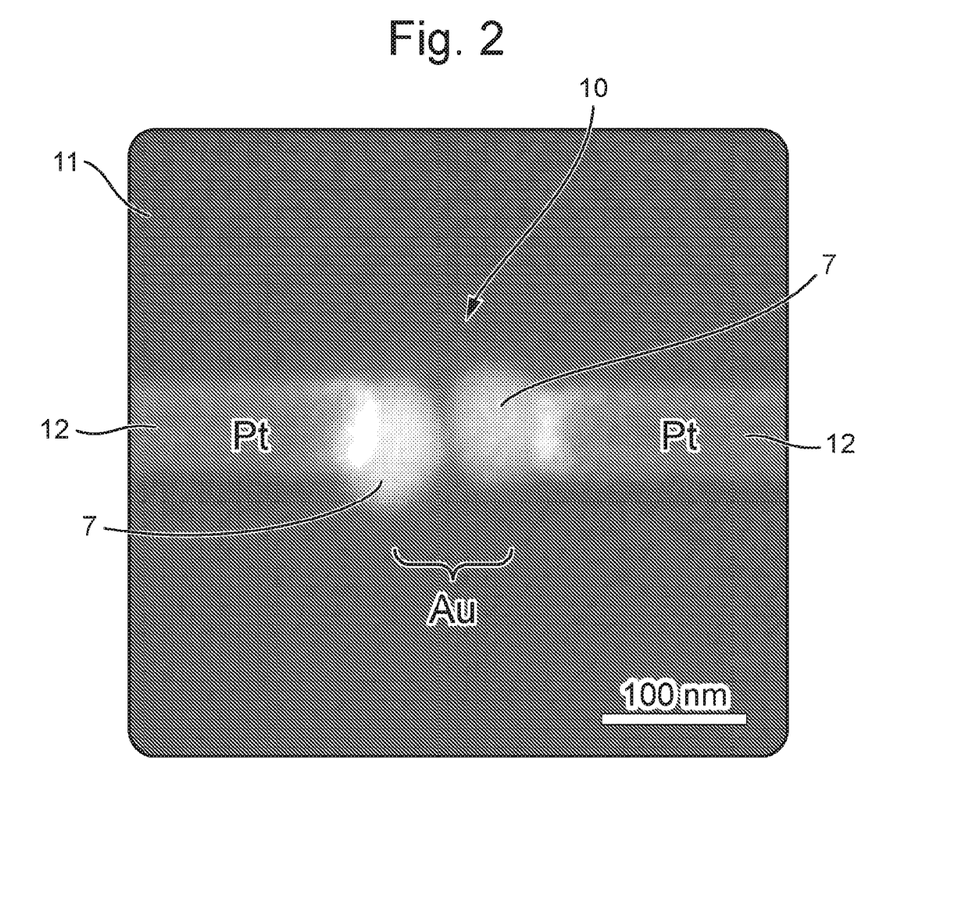
FIG. 2 shows a view of a molecular electronic device deposited on a substrate.

FIG. 2 shows a view (imaged by a scanning electron microscope) of a molecular electronic device 10 (with its gold nanoparticle contacts 7 particularly visible) deposited on a substrate 11 and connected up with platinum wires 12. To achieve this, first the assembled molecular electronic devices 10 are deposited on a silicon dioxide on silicon substrate 11, e.g. by evaporating the aqueous buffer (salty water) in which the molecular electronic devices were assembled. Electron beam-induced deposition of platinum (having a resolution of a few nanometres) is then used to deposit platinum wires 12 on the substrate to make electrical connections to the gold nanoparticle contacts 7.

Figure 3A:
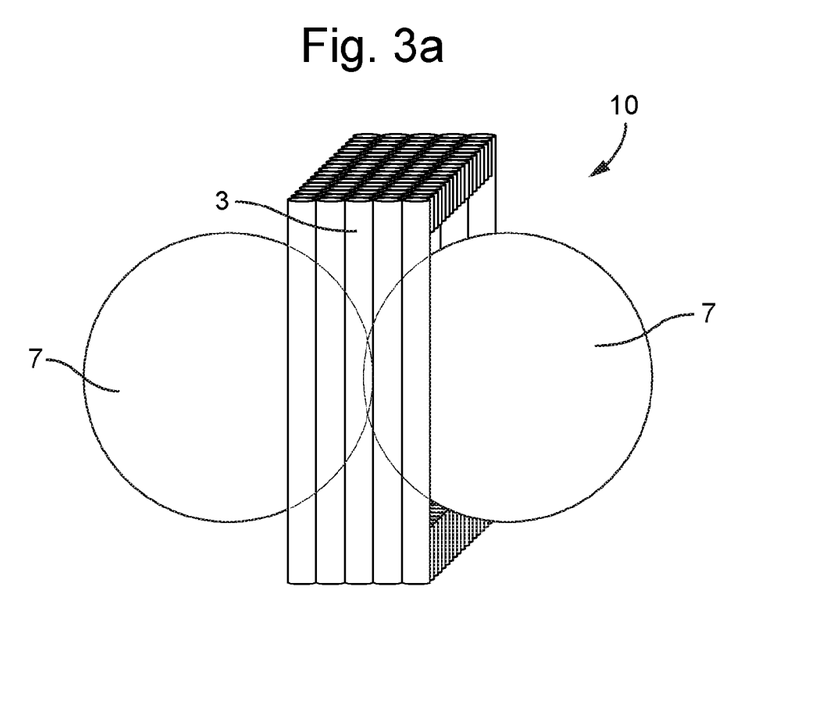
FIGS. 3a and 3b show schematically a molecular electronic device according to two embodiments of the present invention.
Figure 3B:
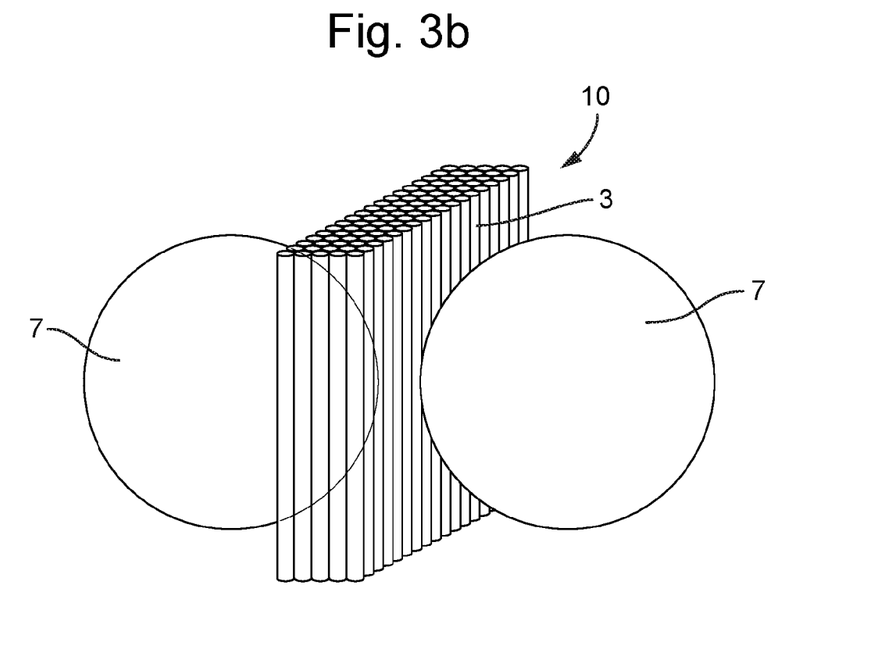

FIGS. 3a and 3b show schematically two embodiments of the molecular electronic device 10. As shown in FIGS. 3a and 3b, the DNA framework 3 may be designed to control the separation of the gold nanoparticles 7 in the molecular electronic device 10, and thus the distance from each of the gold nanoparticles 7 to the molecular electronic component (not shown in FIGS. 3a and 3b) of the molecular electronic device 10. In FIG. 3a, the DNA framework 3 has three layers of double stranded polynucleotides between the two gold nanoparticles 7, giving a separation of approximately 5.2 nm, while in FIG. 3b the DNA framework 3 only has a single layer giving a separation of approximately 1.7 nm between the gold nanoparticles 7.

Figure 4A:
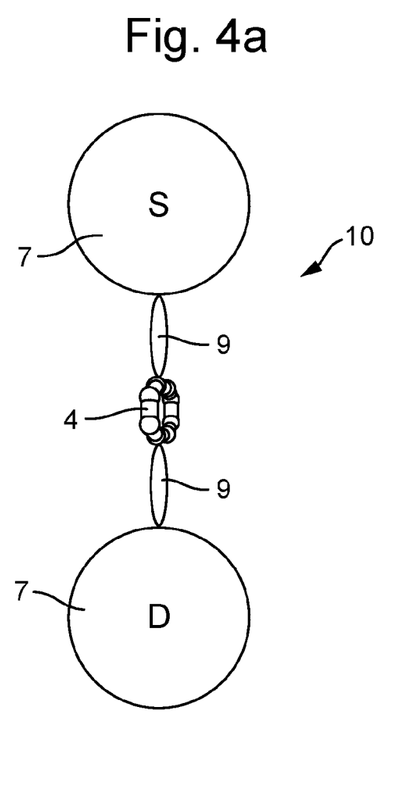
FIGS. 4a and 4b show schematically two embodiments of the molecular electronic device.
Figure 4B:
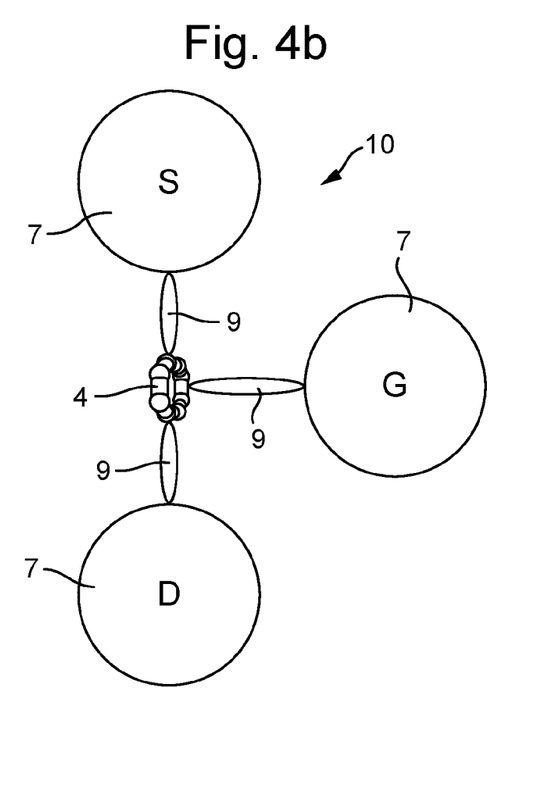

FIGS. 4a and 4b show schematically two embodiments of the molecular electronic device 10. In FIGS. 4a and 4b the DNA framework is not shown for the purposes of clarity. FIG. 4a shows an embodiment in which the molecular electronic device 10 has two gold nanoparticle contacts 7 (a source and a drain) attached to the molecular electronic component 4 via respective conducting oligomers 9. FIG. 4b shows an embodiment in which the molecular electronic device 10 has three gold nanoparticle contacts 7 (a source, a drain and a gate) attached to the molecular electronic component 4 via respective conducting oligomers 9 which act as current leads and an electrostatic gate respectively. To provide an electrostatic coupling between the conducting oligomer 9 of the gate terminal and the (e.g. channel) of the molecular electronic component 4 (e.g. a field effect transistor), the chemical structure of the molecular electronic component 4 is insulating at the location where it is attached to the conducting oligomer 9).

It will be seen from the above that in at least preferred embodiments, the present invention provides a molecular electronic device and a method of assembling a molecular electronic device. The DNA framework in the molecular electronic device helps to provide an atomically precise breadboard for the assembly of molecular components. The use of a DNA framework helps to ensure that each device contains one molecular electronic component, held precisely in place, eliminating uncertainty in the number, nature and orientation of bound molecules that is inherent to current assembly methods for molecular electronic devices.

The use of a DNA framework also helps to provide a high yield process which is reliable, repeatable, reproducible and scalable, and therefore produces working devices with confidence.

The invention claimed is:

1. A molecular electronic device comprising:
   a framework comprising a plurality of double stranded polynucleotide helices arranged to form a plurality of layers of double stranded polynucleotide helices;
   wherein the plurality of double stranded polynucleotide helices are arranged to form a plurality of layers of double stranded polynucleotide helices such that the arrangement of the plurality of layers provides an assembled framework having a three-dimensional shape, wherein the three-dimensional shape has two dimensions in a plane parallel to each layer of the plurality of layers and a third dimension in a plane perpendicular to the plurality of layers, wherein said third dimension is greater than a thickness of any one layer of the plurality of layers;
   one or more molecular electronic components each connected to one or more of the plurality of double stranded polynucleotide helices; and
   one or more electrical contacts each connected to one or more of the plurality of double stranded polynucleotide helices,
   wherein a number of layers of double stranded polynucleotide helices of the plurality of layers of double stranded polynucleotide helices are located between an electrical contact of the one or more electrical contacts and a molecular electronic component of the one or more molecular electronic components,
   wherein the distance between the electrical contact of the one or more electrical contacts and the molecular electronic component of the one or more molecular electronic components is predetermined by the number of layers of double stranded polynucleotide helices such that the number of layers of double stranded polynucleotide helices sets the distance between the electrical contact of the one or more electrical contacts and the molecular electronic component of the one or more molecular electronic components; and
   wherein the one or more molecular electronic components and the one or more electrical contacts are located with respect to the framework and with respect to each other so as to form a coupling between the one or more electrical contacts and the one or more molecular electronic components.

2. The molecular electronic device as claimed in claim 1, wherein the molecular electronic device comprises a plurality of molecular electronic components, and the plurality of molecular electronic components are each connected to one or more of the plurality of polynucleotides such that two or more of the plurality of molecular electronic components are located with respect to the framework and with respect to each other so as to form a coupling between the two or more molecular electronic components.

3. The molecular electronic device as claimed in claim 1, wherein the one or more molecular electronic components have a molecular mass between 100 Dalton (Da) and 10,000 Da.

4. The molecular electronic device as claimed in claim 1, wherein the one or more molecular electronic components comprises a magnetic heterometallic ring, an antiferromagnetic ring, a quantum dot and/or a rotaxane.

5. The molecular electronic device as claimed in claim 1, wherein the plurality of double stranded polynucleotides comprises a longer scaffold polynucleotide and a plurality of shorter staple polynucleotides, wherein the shorter staple polynucleotides are arranged to link together different parts of the longer scaffold polynucleotide to provide the layers of double stranded polynucleotide helices which in turn forms the shape of the assembled framework.

6. The molecular electronic device as claimed in claim 1, wherein the shape of the assembled framework formed by the arrangement of the plurality of layers od doubled stranded polynucleotide helices comprises one or more depressions arranged to locate the one or more electrical contacts respectively.

7. The molecular electronic device as claimed in claim 1, wherein the molecular electronic device comprises one or more connecting polynucleotides attached to the one or more molecular electronic components and arranged to connect the one or more molecular electronic components to the one or more of the plurality of polynucleotides forming the framework.

8. The molecular electronic device as claimed in claim 1, wherein the one or more molecular electronic components are attached directly to the one or more of the plurality of polynucleotides forming the framework.

9. The molecular electronic device as claimed in claim 1, wherein the one or more molecular electronic components are attached to the one or more of the plurality of polynucleotides forming the framework or to one or more connecting polynucleotides via one or more respective covalent bonds.

10. The molecular electronic device as claimed in claim 1, wherein the one or more electrical contacts consist of one or more gold nanoparticles having a diameter of between 20 nm and 100 nm.

11. The molecular electronic device as claimed in claim 1, wherein the molecular electronic device comprises one or more connecting polynucleotides attached to the one or more electrical contacts and arranged to connect the one or more electrical contacts to the one or more of the plurality of polynucleotides forming the framework.

12. The molecular electronic device as claimed in claim 1, wherein the molecular electronic device comprises between 1 and 10,000 connecting polynucleotides attached to the one or more electrical contacts and the plurality of polynucleotides forming the framework comprises between 1 and 100 polynucleotides each comprising a single-stranded section that are hybridized with the plurality of connecting polynucleotides attached to the one or more electrical contacts.

13. The molecular electronic device as claimed in claim 1, wherein the one or more electrical contacts are attached to the one or more of the plurality of polynucleotides forming the framework or to one or more connecting polynucleotides via one or more respective covalent bonds.

14. The molecular electronic device as claimed in claim 1, wherein the coupling comprises a conductive coupling or the coupling comprises a highly resistive coupling.

15. The molecular electronic device as claimed in claim 1, wherein the coupling is formed by controlling the distance between the one or more molecular electronic components and one or more other molecular electronic components and/or the one or more electrical contacts, or the coupling is formed through the formation of a covalent or other chemical bond between the one or more molecular electronic components and the one or more electrical contacts.

16. The molecular electronic device as claimed in claim 1, wherein the molecular electronic device comprises one or more conducting oligomers or other substantially electrically conducting molecules arranged between the one or more molecular electronic components and the one or more electrical contacts to form the coupling between the one or more molecular electronic components and the one or more electrical contacts, or to form the coupling between two or more molecular electronic components.

17. The molecular electronic device as claimed in claim 16, wherein the one or more conducting oligomers or other substantially electrically conducting molecules are attached to the one or more molecular electronic components and/or to the one or more electrical contacts via respective covalent bonds.

18. A method of assembling a molecular electronic device, the method comprising:
assembling a framework to provide an assembled framework having a three-dimensional shape, wherein the assembled framework comprises a plurality of double stranded polynucleotide helices arranged to form a plurality of layers of double stranded polynucleotide helices that provides the three-dimensional shape, wherein the three-dimensional shape has two dimensions in a plane parallel to each layer of the plurality of layers and a third dimension in a plane perpendicular to the plurality of layers, wherein said third dimension is greater than a thickness of any one layer of the plurality of layers;
connecting one or more electrical contacts to one or more of the plurality of double stranded polynucleotide helices;
wherein a number of layers of double stranded polynucleotide helices of the plurality of layers of double stranded polynucleotide helices are located between an electrical contact of the one or more electrical contacts and a molecular electronic component of the one or more molecular electronic components; and
wherein the distance between the electrical contact of the one or more electrical contacts and the molecular electronic component of the one or more molecular electronic components is predetermined by the number of layers of double stranded polynucleotide helices such that the number of layers of double stranded polynucleotide helices sets the distance between the electrical contact of the one or more electrical contacts and the molecular electronic component of the one or more molecular electronic components; and
wherein the one or more molecular electronic components and the one or more electrical contacts are located with respect to the framework and with respect to each other so as to form a coupling between the one or more electrical contacts and the one or more molecular electronic components.

19. The method as claimed in claim 18, wherein the method comprises one of more of the steps of:
i) connecting a plurality of molecular electronic components to one or more of the plurality of polynucleotides, and wherein the plurality of molecular electronic components are each connected to one or more of the plurality of polynucleotides such that two or more of the plurality of molecular electronic components are located with respect to the framework and with respect to each other so as to form a coupling between the two or more molecular electronic components;
ii) assembling the framework, wherein the plurality of double stranded polynucleotides of the framework comprises a longer scaffold polynucleotide and a plurality of shorter staple polynucleotides, and the step of assembling the framework comprises linking together different parts of the longer scaffold polynucleotide using the plurality of shorter staple polynucleotides to provide the layers of double stranded polynucleotides helices which in turn forms the shape of the assembled framework;
iii) annealing the plurality of polynucleotides to assemble the framework;
iv) attaching one or more connecting polynucleotides to the one or more molecular electronic components, and connecting the one or more molecular electronic components to the one or more of the plurality of polynucleotides forming the framework to locate the one or more molecular electronic components with respect to the framework using the one or more connecting polynucleotides attached to the one or more molecular electronic components, and/or attaching one or more connecting polynucleotides to the one or more electrical contacts, and connecting the one or more electrical contacts to the one or more of the plurality of polynucleotides forming the framework to locate the one or more electrical contacts with respect to the framework using the one or more connecting polynucleotides attached to the one or more electrical contacts;
v) assembling the molecular electronic device in an aqueous solution;
vi) depositing the molecular electronic device on a substrate.

20. A method of assembling a plurality of molecular electronic devices, the method comprising:

assembling a plurality of frameworks to provide a plurality of assembled frameworks, each assembled framework having a three-dimensional shape, wherein each assembled framework comprises a plurality of double stranded polynucleotide helices arranged to form a plurality of layers of double stranded polynucleotide helices that provides the three-dimensional shape, wherein the three-dimensional shape has two dimensions in a plane parallel to each layer of the plurality of layers and a third dimension in a plane perpendicular to the layers, wherein said third dimension is greater than a thickness of any one layer of the plurality of layers;

for each of the plurality of frameworks the method comprises:
- connecting one or more molecular electronic components to one or more of the plurality of double stranded polynucleotide helices; and
- connecting one or more electrical contacts to one or more of the plurality of double stranded polynucleotide helices;
- wherein a number of layers of double stranded polynucleotide helices of the plurality of layers of double stranded polynucleotide helices are located between an electrical contact of the one or more electrical contacts and a molecular electronic component of the one or more molecular electronic components; and
- wherein the distance between the electrical contact of the one or more electrical contacts and the molecular electronic component of the one or more molecular electronic components is predetermined by the number of layers of double stranded polynucleotide helices such that the number of layers of double stranded polynucleotide helices sets the distance between the electrical contact of the one or more electrical contacts and the molecular electronic component of the one or more molecular electronic components; and
- wherein the one or more molecular electronic components and the one or more electrical contacts are located with respect to the framework and with respect to each other so as to form a coupling between the one or more electrical contacts and the one or more molecular electronic components.

* * * * *